US010463821B2

(12) United States Patent
White et al.

(10) Patent No.: US 10,463,821 B2
(45) Date of Patent: Nov. 5, 2019

(54) SUCTION CATHETER ADAPTOR

(71) Applicant: Vyaire Medical Consumables LLC, Yorba Linda, CA (US)

(72) Inventors: Dennis White, Yorba Linda, CA (US); Haojun Fu, Yorba Linda, CA (US)

(73) Assignee: Vyaire Medical Consumables LLC, Yorba Linda, CA (US)

( * ) Notice: Subject to any disclaimer, the term of this patent is extended or adjusted under 35 U.S.C. 154(b) by 345 days.

(21) Appl. No.: 15/354,860

(22) Filed: Nov. 17, 2016

(65) Prior Publication Data

US 2017/0143921 A1 May 25, 2017

Related U.S. Application Data

(60) Provisional application No. 62/257,630, filed on Nov. 19, 2015.

(51) Int. Cl.
*A61M 16/04* (2006.01)
*A61M 16/20* (2006.01)
(Continued)

(52) U.S. Cl.
CPC .... *A61M 16/0463* (2013.01); *A61M 16/0833* (2014.02); *A61M 16/208* (2013.01); *A61M 25/01* (2013.01); *A61M 39/10* (2013.01); *A61M 39/24* (2013.01); *A61M 2039/1077* (2013.01); *A61M 2039/226* (2013.01); *A61M 2039/2426* (2013.01)

(58) Field of Classification Search
CPC .......... A61M 16/0463; A61M 16/0833; A61M 25/01; A61M 39/10; A61M 16/208; A61M 2039/2426; A61M 2039/1077
See application file for complete search history.

(56) References Cited

U.S. PATENT DOCUMENTS 4,917,668 A 4/1990 Haindl
5,333,607 A 8/1994 Kee et al.
(Continued)

FOREIGN PATENT DOCUMENTS

EP 0875262 A2 11/1998
JP 2012200569 10/2012

OTHER PUBLICATIONS

International Search Report and Written Opinion for Application No. PCT/US2016/062553, dated Feb. 17, 2017, 17 pages.

*Primary Examiner* — Bradley J Osinski
(74) *Attorney, Agent, or Firm* — Morgan, Lewis & Bockius LLP

(57) ABSTRACT

An exemplary suction catheter adaptor includes an adaptor body having a passageway between a proximal end and a distal end of the adaptor body. The proximal end of the adaptor body receives an instrument and, when coupled with an airway adaptor having a valve within a passageway between a proximal end and a distal end of the airway adaptor, the distal end of the adaptor body deflects the valve to permit the instrument to be advanced or retracted through the valve. A seal within the passageway of the adaptor body is biased to engage the valve during advancement of an instrument toward the valve, and the seal is disengaged when the instrument is retracted away from the valve. The valve, when not engaged, occludes the passageway between a proximal end and a distal end of the airway adaptor.

19 Claims, 12 Drawing Sheets

(51) Int. Cl.

| | |
|---|---|
| ***A61M 39/10*** | (2006.01) |
| ***A61M 39/24*** | (2006.01) |
| ***A61M 25/01*** | (2006.01) |
| ***A61M 16/08*** | (2006.01) |
| *A61M 39/22* | (2006.01) |

(56) References Cited

U.S. PATENT DOCUMENTS

| | | | | |
|---|---|---|---|---|
| 5,582,161 | A | 12/1996 | Kee | |
| 5,664,594 | A * | 9/1997 | Kee .................. | A61M 16/0463 134/166 R |
| 5,911,710 | A * | 6/1999 | Barry ................ | A61M 39/0693 604/167.04 |
| 7,152,603 | B1 * | 12/2006 | Crump ............. | A61M 16/0463 128/207.14 |
| 2010/0269829 | A1 | 10/2010 | Hansmann et al. | |

* cited by examiner

FIG. 1

SUCTION CATHETER ADAPTOR

CROSS-REFERENCE TO RELATED APPLICATION

This application claims the benefit of U.S. Provisional Application No. 62/257,630, filed on Nov. 19, 2015, which is hereby incorporated by reference.

TECHNICAL FIELD

The present disclosure generally relates to breathing circuit airway adaptors, artificial airways, and more particularly to suction catheter adaptors and methods of using the same.

BACKGROUND

Ventilators and related breathing circuits assist a patient with breathing. For example, during surgery and other medical procedures, a ventilator provides respiratory gases to the patient. The ventilator provides respiratory gases into the patient's respiratory tract via an artificial airway tube, such as a tracheostomy tube, endotracheal tube, etc. While some breathing circuits establish a single, direct fluid connection between the ventilator and the artificial airway, in many instances, caregivers desire the ability to introduce instruments and/or devices into the breathing circuit, for example, to insert instruments for visualization or related procedures, or to aspirate fluid or secretions from the patient's airway. Accordingly, an airway adaptor permits coupling of a patient's artificial airway to a ventilator while also facilitating the introduction of other instruments into the artificial airway.

Instruments, such as a suction catheter, are inserted through an access port or opening of the airway adaptor and into the artificial airway of the patient. In some instances, the airway adaptor includes a valve to obstruct the access port and isolate the breathing circuit when the instrument is retracted from the artificial airway. Because the breathing circuit is under positive pressure with respect to the ambient environment, isolation of the breathing circuit prevents substances from transferring from the breathing circuit into the ambient environment.

SUMMARY

To insert an instrument into the artificial airway, the valve is bypassed as the instrument is advanced through the airway adaptor. In some instances, the instrument advanced through the airway adaptor is fragile and subject to buckling or bending. For example, suction catheter tubes for neonatal patients comprise a soft material with a small cross-sectional width. When the suction catheter is advanced through the airway adaptor to open the valve, engagement against the closed valve causes the suction catheter tube to buckle or bend. In some aspects, portions of the valve that are biased to permit the suction catheter tube to be inserted through the airway adaptor exert a force onto the tube that cause the tube wall to buckle or bend.

The disclosed suction catheter adaptor can couple with an airway adaptor to bias or urge the valve and permit advancing a suction catheter, or other instrument or device, through the airway adaptor and into an artificial airway.

Some aspects of the present disclosure provide a suction catheter adaptor assembly comprising: an adaptor body comprising an inner surface defining a passageway between a proximal end and a distal end of the adaptor body, the distal end of the adaptor body configured to couple with an airway adaptor; and the airway adaptor comprising (i) an inner surface defining a passageway between a proximal end and a distal end of the airway adaptor, the distal end configured to couple with an artificial airway, and (ii) a valve configured to occlude the passageway, the valve comprising a resiliently flexible annular member and a plurality of valve segments separated by a slit; wherein, the distal end of the adaptor body, when received into the proximal end of the airway adaptor, engages the ridge to bias the plurality of valve segments toward the distal end of the airway adaptor such that the slit is expanded to fluidly couple the airway adaptor passageway and adaptor body passageway through the valve.

In some aspects of the present disclosure, the adaptor body comprises a seal across the passageway proximal to the adaptor body distal end. In some instances, the seal comprises a radial flange with an access aperture, the access aperture of the seal having an inner surface with a cross-sectional width that is equal to or less than a cross-sectional width of an outer surface of a suction catheter inserted through the access aperture. In some embodiments of the present disclosure, the valve comprises a plurality of slits. In some embodiments, the plurality of valve segments extends radially inward from the annular member. Some embodiments provide, the annular member comprises an annular continuous ridge.

Some aspects of the present disclosure provides a suction catheter adaptor assembly comprising: an adaptor body having a seal, the adaptor body comprising an inner surface defining a passageway between a proximal end and a distal end of the adaptor body, the distal end of the adaptor body configured to couple with an airway adaptor, the seal configured to extend across the passageway, the seal comprising (i) a radial flange having an access aperture, and (ii) a plunger comprising a cylindrical shaft extending distally from the radial flange toward the distal end of the adaptor body and terminating in an annular edge, wherein deflection of the radial flange toward the distal end of the adaptor body moves the plunger away from the proximal end of the adaptor body; and the airway adaptor comprising an inner surface defining a passageway between a proximal end and a distal end of the airway adaptor, the distal end configured to couple with an artificial airway, and a valve configured to occlude the passageway, the valve comprising a resiliently flexible annular member and a plurality of valve segments separated by a slit; wherein, when the adaptor body is coupled with the proximal end of the airway adaptor, deflection of the radial flange toward the distal end of the adaptor body engages the annular edge of the plunger against the annular member of the airway adaptor valve, such that the plurality of valve segments are deflected toward the distal end of the airway adaptor to open the slit and fluidly couple the airway adaptor passageway and adaptor body passageway.

In some implementations, deflection of the radial flange toward the proximal end of the adaptor body retracts the plunger toward the proximal end of the adaptor body. In some embodiments, the access aperture of the seal comprises an inner surface with a cross-sectional width that is equal to or less than a cross-sectional width of an outer surface of a suction catheter inserted through the access aperture. In some instances, retraction of a suction catheter inserted through the access aperture of the seal toward the proximal end of the adaptor body retracts the head from the annular member of the valve. In some implementations, retraction of a suction catheter inserted through the valve and towards the proximal end of the adaptor body shifts the valve segments toward the adaptor body.

In some instances of the present disclosure, the adaptor body comprises a radial port between the seal and the distal end of the adaptor body, the radial port having a passageway fluidly coupled to the passageway of the adaptor body. In some instances, a fluid aperture extends through a wall of the cylindrical shaft such that the radial port is fluidly coupled to an inner surface of the cylindrical shaft. In some implementations, a plurality of fluid apertures extends through the wall about a circumference of the cylindrical shaft. In some embodiments, the outside surface of the cylindrical shaft is concaved, forming a concave channel about a circumference of the shaft. In some aspects, the concave channel, and a fluid aperture extending through a wall of the cylindrical shaft are axially aligned between the radial flange and the annular edge. Some aspects provide that the annular edge comprises an annular head, the annular head having a cross-sectional thickness greater than a cross-sectional thickness of a wall of the cylindrical shaft.

According to some implementations, the present disclosure provides a method of fluidly coupling a suction catheter using a suction catheter adaptor, comprising: advancing an adaptor body into a passageway of an airway adaptor such that a distal end of the adaptor body engages a valve within the airway adaptor, the valve comprising a resiliently flexible annular member and a plurality of valve segments defined by a slit; and advancing the distal end of the adaptor body distally against the annular member such that the plurality of valve segments are deflected distally away from the distal end of the adaptor body to fluidly couple a passageway through the adaptor body with the airway adaptor distally of the valve. Some embodiments provide advancing a suction catheter through the passageway of the adaptor body and the passageway of the airway adaptor, the suction catheter being permitted to pass between the biased plurality of valve segments.

According to some implementations, the present disclosure provides a method of fluidly coupling a suction catheter using a suction catheter adaptor, comprising: coupling a distal end of an adaptor body with a passageway of an airway adaptor having a valve comprising a plurality of valve segments defined by a slit, the adaptor body comprising seal having a radial flange and a plunger, the plunger comprising a cylindrical shaft extending from the radial flange toward the distal end of the adaptor body and terminating in an annular edge; biasing the radial flange toward the distal end of the adaptor body to move the plunger into engagement with the valve; and advancing the plunger against the valve to bias the plurality of valve segments away from the adaptor body. Some embodiments provide biasing the radial flange by advancing a suction catheter through an access aperture of the seal, wherein the access aperture comprises an inner surface with a cross-sectional width is equal to or less than a cross-sectional width of an outer surface of the suction catheter.

Additional features and advantages of the subject technology will be set forth in the description below, and in part will be apparent from the description, or may be learned by practice of the subject technology. The advantages of the subject technology will be realized and attained by the structure in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 1 illustrates a breathing circuit connected to a patient, in accordance with aspects of the present disclosure.

DETAILED DESCRIPTION

Figure 2A:
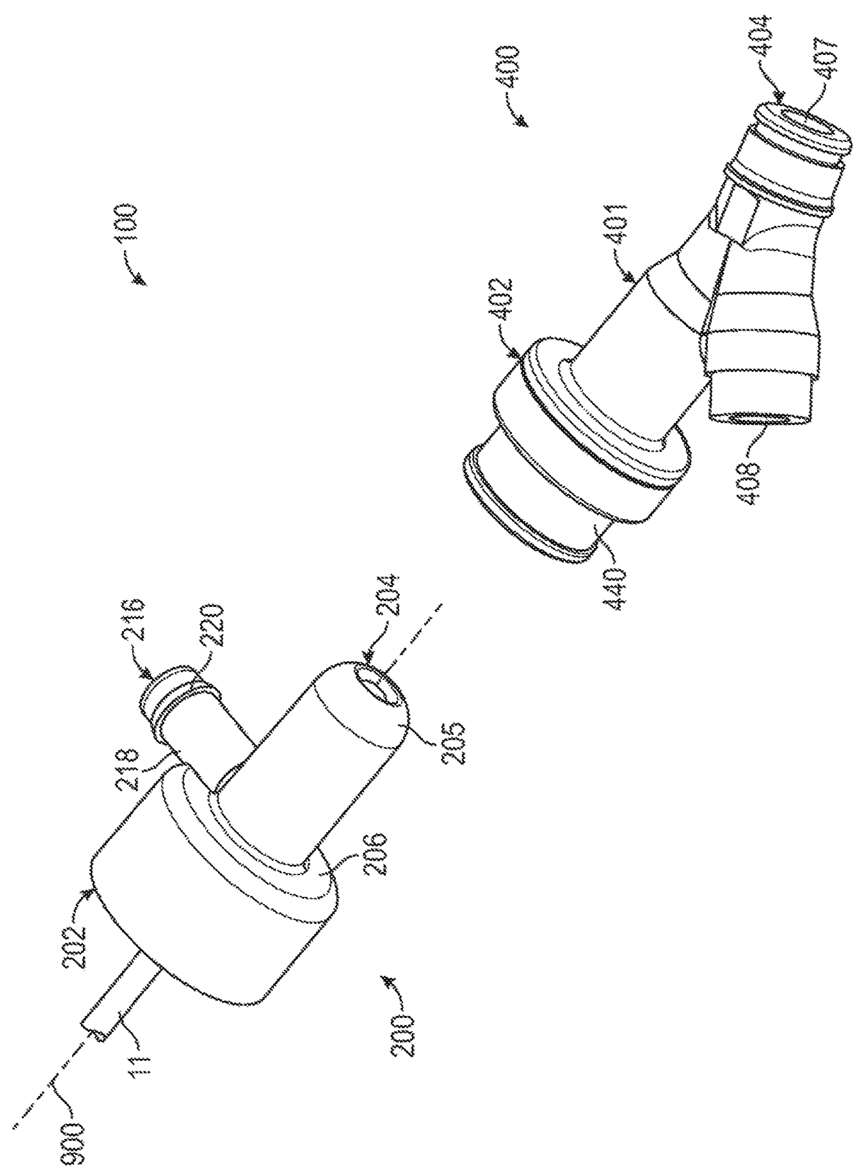
FIG. 2A illustrates a perspective view of a suction catheter adaptor, in accordance with aspects of the present disclosure.

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

Figure 1:
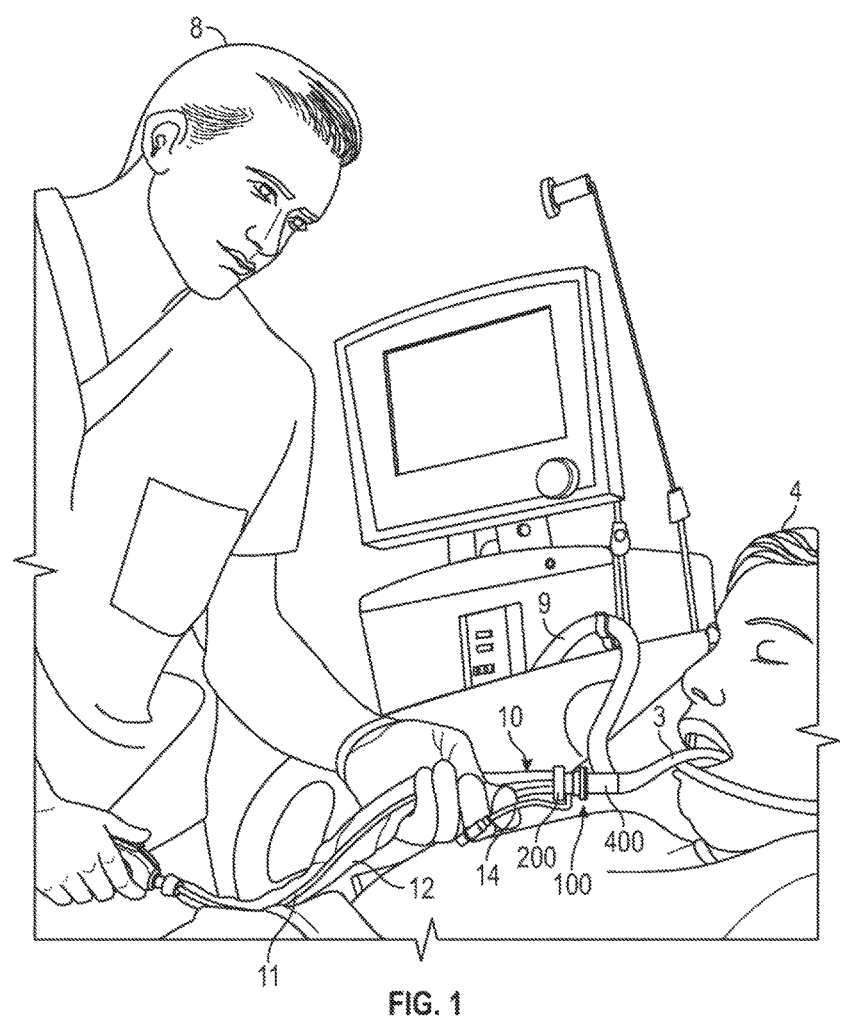

Referring to FIG. 1, a breathing circuit coupled with a patient 4 is illustrated. The breathing circuit includes an airway adaptor 400 coupled between a ventilator 9 and the artificial airway 3 of the patient 4. A caregiver 8 is illustrated using an instrument 10 inserted into the breathing circuit. The instrument 10 can be coupled to the breathing circuit through a suction catheter adaptor 100 having an adaptor body 200 coupled to the airway adaptor 400. The airway adaptor 400 can include a valve configured to obstruct a passageway therethrough. Some aspects of the suction catheter adaptor 100 permit the instrument 10 and adaptor body 200 to be coupled and decoupled from the artificial airway 3 to engage and disengage the valve, respectively. The valve can be engaged and urged when the adaptor body 200 is coupled to the airway adaptor 400 to permit the instrument 10 to be advanced and retracted through the suction catheter adaptor 100 while minimizing stress on the instrument 10 by the valve in the airway adaptor 400. In some aspects, the suction catheter adaptor 100 minimizes stress on the instrument 10 by reducing torsional, shear, and tensile stress, between the instrument 10 and the valve.

Figure 2B:
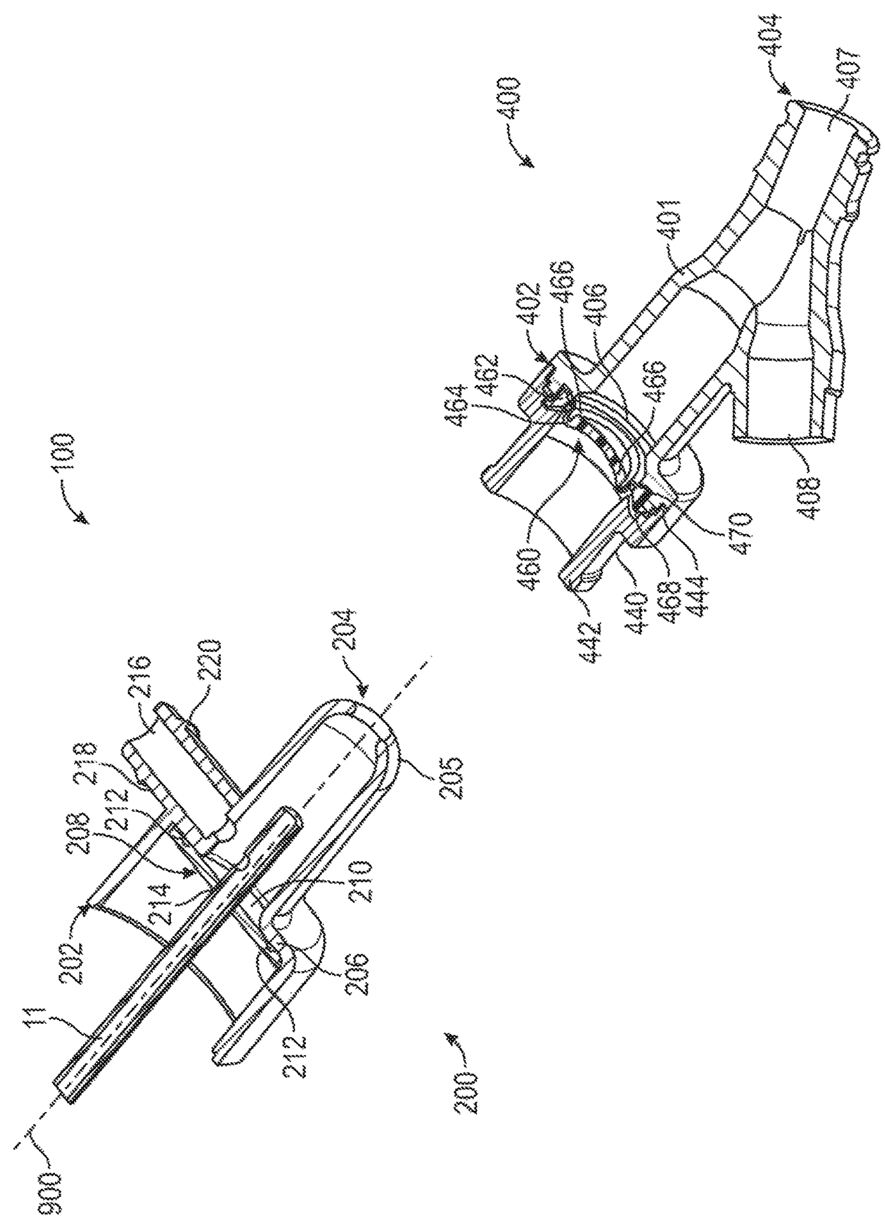
FIG. 2B illustrates a cross-sectional perspective view of the suction catheter adaptor of FIG. 2A.
Figure 3:
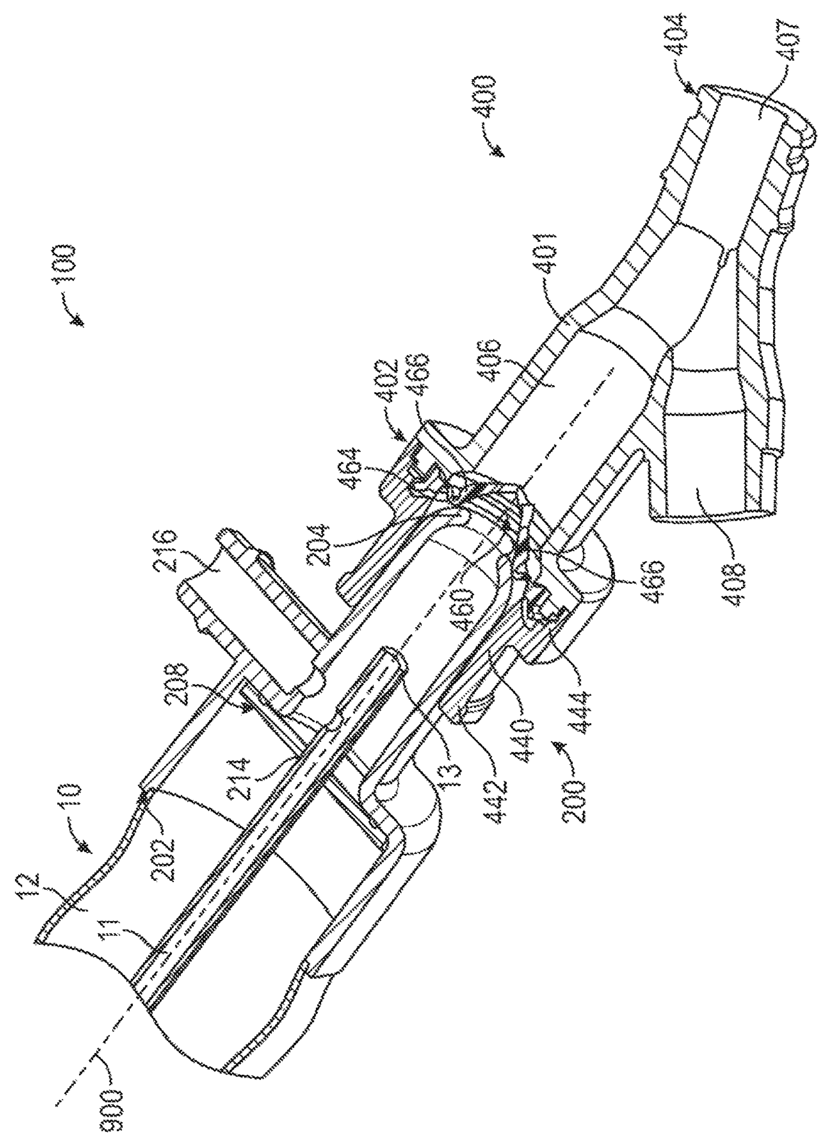
FIG. 3 illustrates a cross-sectional perspective view of a suction catheter adaptor, in accordance with aspects of the present disclosure.
Figure 4:
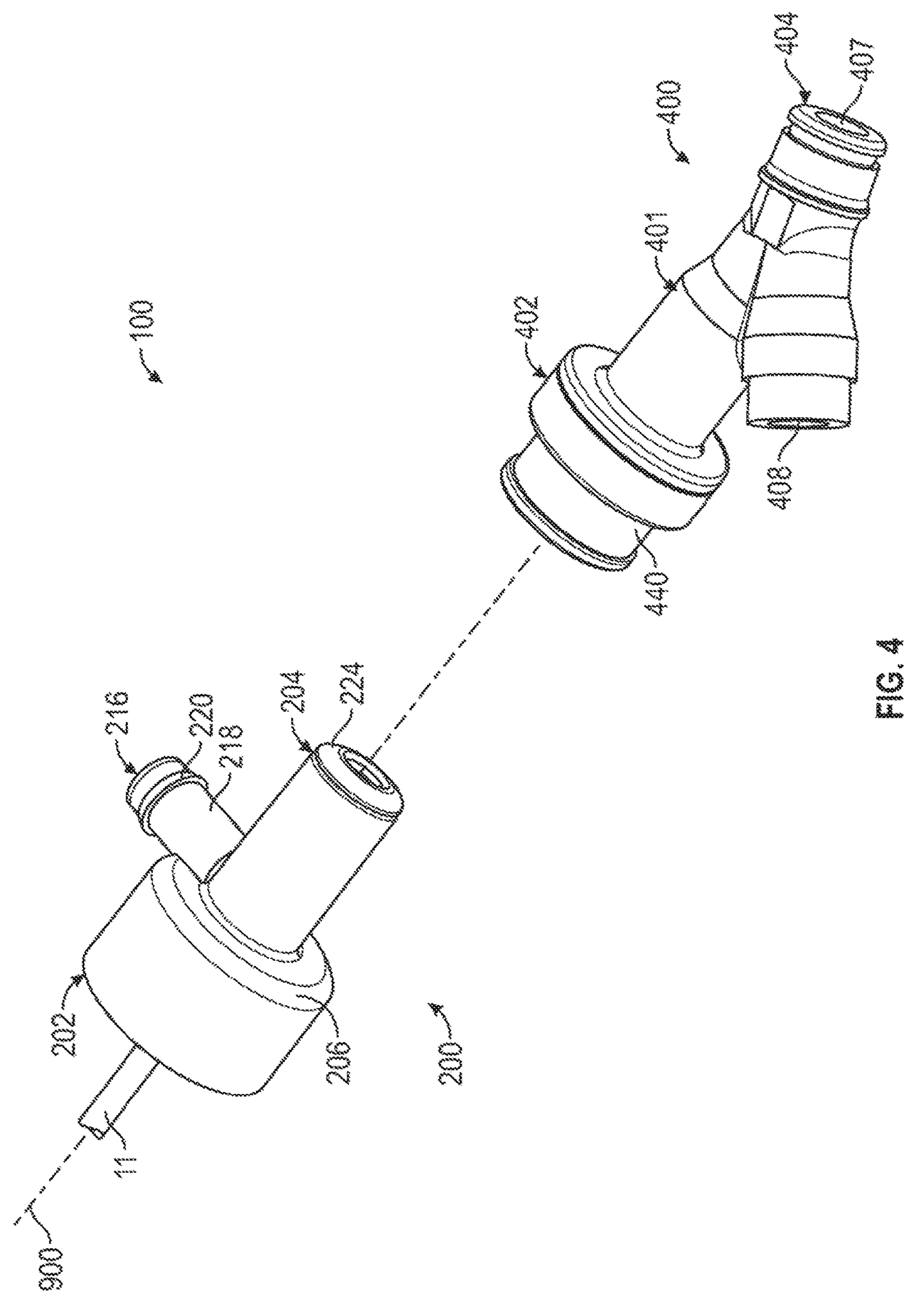
FIG. 4 illustrates a perspective view of a suction catheter adaptor, in accordance with aspects of the present disclosure.

FIGS. 2A-3 illustrate embodiments of the suction catheter adaptor 100. The suction catheter adaptor 100 includes an adaptor body 200 comprising a proximal end portion configured to couple with an instrument, a distal end portion configured to couple with an airway adaptor, and a passageway between the proximal and distal end portions. In some aspects, the adaptor body 200 comprises a proximal end 202 configured to couple with an instrument, an opposing distal end 204 configured to couple with an airway adaptor 400, and a longitudinal axis 900 between the proximal end 202 and the distal end 204. An inner surface of the adaptor body 200 defines a passageway extending from the proximal end 202 to the distal end 204. A portion of the adaptor body 200 can comprise a cross-sectional profile that tapers toward any of the proximal and distal end portions. In some embodiments, an outer surface the adaptor body 200 tapers from the proximal end 202 toward the distal end 204. The distal end 204 of the adaptor body 200 can comprise a narrowing cross-section forming a tapered or convex tip 205.

For clarity, a portion of an instrument coupled to the adaptor body 200 is illustrated, while the remainder of the instrument is not visible in some figures. Specifically, a suction catheter tube 11 is illustrated partially inserted into the adaptor body 200 while the suction catheter sheath 12 is only visible in FIG. 3. Connection of the suction catheter adaptor 100 is described herein with reference to a suction catheter; however, suction catheter adaptor 100 may be coupled to any instrument or device having similar features.

In some aspects, a portion of the inner surface of the adaptor body 200, between the proximal end 202 and the distal end 204, extends radially inward at a circumferential ledge 206. In some aspects, a cross-sectional width of the inner surface between the proximal end 202 and the circumferential ledge 206 is greater than a cross-sectional width of the inner surface between the circumferential ledge 206 and the distal end 204.

Referring to FIG. 2B, the adaptor body 200 can include a seal 208 configured to intersect or obstruct a portion of the passageway. The seal 208 can be positioned in the passageway, between the proximal end 202 and the distal end 204. In some aspects, the seal 208 can extend across or intersect the passageway. The seal 208 is preferably positioned along a proximal portion of the passageway, between the proximal end 202 and the circumferential ledge 206, or along a distal portion of the passageway, between the circumferential ledge 206 and the distal end 204. The seal 208 can be separated, or spaced apart, from the distal end 204 to form a wash zone in the adaptor body 200, between the seal 208 and the distal end 204.

The seal 208 can include a radial flange 210 extending radially outward. The radial flange 210 can extend toward an inner surface of the adaptor body 200 such that the seal 208 intersects the passageway. The radial flange 210 can be coupled to the adaptor body 200 by any of a mechanical fastener, an adhesive, welding, or another coupling method. The radial flange 210 can be seated against or engage the circumferential ledge 206. In some aspects, the seal 208 is coupled to the adaptor body 200 at a connection region 212 between the radial flange 210 and the adaptor body 200. The connection region 212 can be between planar portions of the radial flange 210 and the circumferential ledge 206. The connection region 212 can comprise any of a mechanical fastener, an adhesive, welding, or another coupling method.

The seal 208 can include an access aperture 214 extending through the radial flange 210. The access aperture 214 can be positioned relative to a valve in the airway adaptor 400. The access aperture 214 can be aligned with the longitudinal axis 900 of the adaptor body 200 so that an instrument or device being advanced or retracted through the passageway remains axially aligned with longitudinal axis 900. In some aspects, movement of an instrument or device, transverse to the longitudinal axis 900, is restricted by the seal 208. The access aperture 214 can comprise a cross-sectional width that is approximately equal to or less than the cross-sectional width of the suction catheter tube 11 to create a friction fit between the suction catheter tube 11 and the seal 208.

The adaptor body 200 can include a radial port 216 forming a passageway through a wall of the adaptor body 200, between the seal 208 and the distal end 204. In some aspects, the radial port 216 forms an elongate body 218 extending radially from the outer surface of the adaptor body 200. The radial port 216 is in fluid communication with the passageway of the adaptor body 200. The radial port 216 can be configured to provide a fluid for cleaning operations, described in more detail herein. An outer surface of the elongate body 218 can include an engagement member to permit fluidly coupling the radial port 216 with any of any of a tube, caps, and nozzle. The engagement member can be an outwardly extending ridge 220 for engagement with certain implements such as a fluid tube 14 (FIG. 1).

Still referring to FIGS. 2A-3, the adaptor body 200 can be coupled with an airway adaptor 400. The airway adaptor 400 includes a housing 401 with a plurality of openings and an inner surface defining a passageway between the plurality of openings. In some embodiments, a first opening at a proximal end 402 of the housing 401 forms an access port 406 configured to couple with the adaptor body 200 and receive an instrument, such as the suction catheter tube 11, into the passageway. A second opening at an opposing distal end 404 of the housing 401 forms a respiratory port 407 configured to couple with an artificial airway of a patient. A third opening, between the proximal end 402 and the distal end 404, forms a ventilator port 408 configured to couple with a ventilator to provide respiratory gas to the patient.

The airway adaptor 400 can include a collar 440 having a first end 442, an opposing second end 444, and a passageway between the first end 442 and the second end 444. The second end 444 of the collar 440 is coupled to the proximal end 402 of the housing 401. The second end 444 is configured to couple with the housing 401 using any of a mechanical fastener, an adhesive, welding, or another coupling method. In some embodiments, the collar 440 and housing 401 are formed together as a unitary component. In some aspects, the collar 440 extends along an axial length of the access port 406.

The inner surface of the passageway of the collar 440 can comprise a cross-sectional width that is approximately equal to or greater than the cross-sectional width of the outer surface of the adaptor body 200. The first end 442 of the collar 440 can receive the distal end 204 of the adaptor body 200 into the passageway of the collar 440. In some aspects, the axial length of the collar 440, between the first end 442 and the second end 444, is less than an axial length of the adaptor body received into the passageway of the collar 440. For example, the axial length of the collar 440 can be less than the axial length of the distal portion of the adaptor body 200. In some aspects, when the adaptor body 200 is inserted into the passageway of the collar 440, the distal end 204 of the adaptor body 200 can extend beyond the second end 444 of the collar 440. The collar 440 can be configured such that the distal end 204 of an adaptor body 200, inserted into the passageway of the collar 440, engages a valve of the airway adaptor 400.

Referring to FIGS. 2B and 3, the airway adaptor 400 includes a valve 460 having a first orientation (FIG. 2B) and a second orientation (FIG. 3). In the first orientation, the valve 460 can be configured to fluidly isolate the passageway of the collar 440 from a passageway between the ventilator port 408 and the respiratory port 407. In some embodiments, the passageway of the collar 440 is partially isolated in the first orientation. The valve 460, in the second orientation, can be open to fluidly couple the passageway of the collar 440 with the passageway between the ventilator port 408 and the respiratory port 407. In the second orientation, the valve can permit an instrument or other device to be inserted into the airway adaptor 400.

In some aspects, the valve comprises a rim 462, a resiliently flexible annular member, and a plurality of valve segments 466 that are moveable relative to each other. The valve segments 466 can be separated by any of a cut, an opening, and a slit. In some aspects, the annular member is an annular continuous ridge 464. The rim 462 forms the outer circumferential surfaces of the valve 460. The rim 462 includes a first or leading edge 468 and an opposing second or trailing edge 470. The rim 462 is positioned in a valve retention structure between the collar 440 and the housing 401. In some embodiments, the valve retention structure is an annular channel formed between the second end 444 of the collar 440 and the proximal end 402 of the housing 401. The valve 460 can be retained in the channel such that the leading edge 468 of the rim 462 engages the second end 444 of the collar 440, and the trailing edge 470 of the rim 462 engages the proximal end 402 of the housing 401. However, other valve retention structures are contemplated, for example, a rim-receiving member within the collar 440 proximal to the second end 444, or a series of apertures disposed around a rim 462 of the valve 460 for engagement with a corresponding structure within the housing 401 or collar 440, or for bonding to the housing 401 or collar 440.

In some aspects, the resiliently flexible annular ridge 464 is radially inward from the rim 462. The annular ridge 464 can form a convex surface projecting from a first surface of the valve 460 that is coplanar with the leading edge 468. The plurality of valve segments 466 extend radially inward from the annular ridge 464. The valve segments 466 can be separated by one or more slit that extends through the valve 460, from the first surface to a second surface that is coplanar with the trailing edge 470 of the valve 460. The annular ridge 464 and plurality of valve segments 466 can be configured such that the plurality of valve segments 466 occlude the passageway through the access port 406 when the valve 460 is in the first orientation. In a second orientation, the annular ridge 464 and plurality of valve segments 466 are biased or displaced to permit a fluid, instrument, or other device through the passageway.

Referring to FIG. 3, the adaptor body 200 is coupled with the airway adaptor 400 by inserting the distal end 204 of the adaptor body 200 through the passageway of the collar 440. As the adaptor body 200 is advanced through the collar 440 toward the proximal end of the housing 401, the tip of the adaptor body 200 can engage and urge the valve 460. In some aspects, the convex tip of the adaptor body 200 engages the annular ridge 464 of the valve 460. The annular ridge 464 can direct a force against the valve 460 toward the valve segments 466. Further advancement of the adaptor body 200 against the annular ridge 464 can urge or deflect the valve segments 466 into the housing 401, thereby placing the valve 460 into the second orientation.

An instrument 10 coupled with the proximal end 402 of the airway adaptor 400 can include a suction catheter tube 11 surrounded by a sheath 12. The suction catheter tube 11 is preferably inserted through the access aperture 214 of the seal 208. During advancement or retraction of the suction catheter tube 11, the seal 208 can guide the suction catheter tube 11 relative to the longitudinal axis 900 of the adaptor body 200 and through the opening provided by the biased valve segments 466 of the valve 460 in the second orientation. The valve 460 may prevent or limit undesired transfer of air from the ventilator through the access port 406 while the suction catheter tube 11 extends through the valve 460. The valve 460 can permit a portion of the instrument 10 to be flushed by fluid from the radial port 216, while preventing the flushing medium from entering the area of the fluid pathway between the valve 460 and respiratory port 407.

To flush the instrument 10, the suction catheter tube 11 can be retracted toward the proximal end 202 of the adaptor body 200 until a portion of the suction catheter tube 11 is in the wash zone of the adaptor body 200, between the seal 208 and the distal end 204. In some aspects, the suction catheter tube 11 is positioned such that a tip 13 of the suction catheter tube is within the wash zone. During retraction of the instrument 10, a friction fit between the seal 208 and the suction catheter tube 11 can dislodge or remove contaminations from the outer surface of the suction catheter tube 11 as the tube is moved through the seal 208. The seal 208 is configured to retain the contamination in the wash zone. A cleaning fluid, such as saline, can be directed through the radial port 216 into the wash zone. A suction force to the suction catheter is applied to remove the cleaning fluid and contamination from the wash zone. Additionally, the suction force to the suction catheter can entrain airflow from the ventilator through the valve and into the wash zone. Agitation of the cleaning fluid with the airflow significantly enhances the effectiveness of the cleaning procedure.

To disconnect the instrument 10 from the airway adaptor 400, the adaptor body 200 can be retracted from the passageway of the collar 440. When the distal end 204 of the adaptor body 200 is retracted from the valve 460 with the tip 13 positioned proximal to the distal end 204, the annular ridge 464 and the valve segments 466 can readily return to an undeflected position in the first orientation to occlude the passageway through the access port 406 of the airway adaptor 400.

Referring now to FIGS. 4-9, embodiments of the suction catheter adaptor 100 are illustrated. The suction catheter adaptor 100 includes an adaptor body 200 comprising a proximal end portion configured to couple with an instrument, a distal end portion configured to couple with an airway adaptor, and a passageway between the proximal and distal end portions. In some aspects, the adaptor body 200 comprises a proximal end 202 configured to couple with an instrument, an opposing distal end 204 configured to couple with an airway adaptor 400, and a longitudinal axis 900 between the proximal end 202 and the distal end 204. An inner surface of the adaptor body 200 defines a passageway extending from the proximal end 202 to the distal end 204. A portion of the adaptor body 200 can comprise a cross-sectional profile that tapers toward any of the proximal and distal end portions. In some aspects, an outer surface the adaptor body 200 tapers from the proximal end 202 toward the distal end 204. A seal, positioned within the passageway of the adaptor body 200, can form an annular edge extending beyond the distal end 204 of the adaptor body 200.

For clarity, a portion of an instrument coupled to the adaptor body 200 is illustrated, while the remainder of the instrument is not visible in some figures. Specifically, a suction catheter tube 11 is illustrated partially inserted into the adaptor body 200 while the suction catheter sheath 12 is only visible in FIG. 6. Connection of the suction catheter adaptor 100 is described herein with reference to a suction catheter; however, suction catheter adaptor 100 may be coupled to any instrument or device having similar feature.

In some aspects, a portion of the inner surface of the adaptor body 200, between the proximal end 202 and the distal end 204, extends radially inward at a circumferential ledge 206. In some aspects, a cross-sectional width of the inner surface between the proximal end 202 and the circumferential ledge 206 is greater than a cross-sectional width of the inner surface between the circumferential ledge 206 and the distal end 204.

Figure 5B:
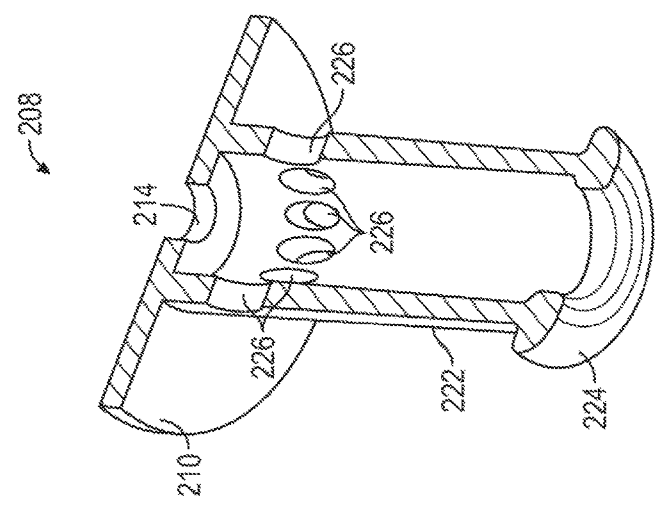
FIG. 5B illustrates a cross-sectional view of the suction catheter adaptor of FIG. 5A.
Figure 5A:
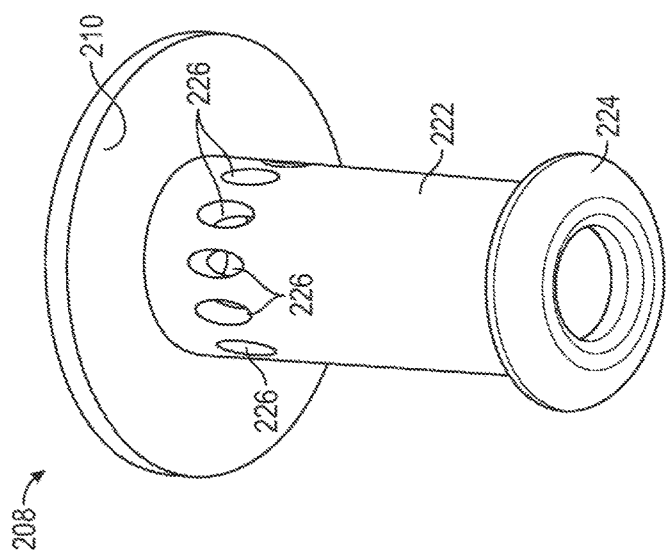
FIG. 5A illustrates a detail view of aspects of the suction catheter adaptor of FIG. 4.

The adaptor body 200 can include a seal 208 illustrated in isolation in FIGS. 5A-5B. The seal 208 can be positioned in the passageway, between the proximal end 202 and the distal end 204. A proximal portion of the seal 208 can comprise a radial flange 210 having a first planar surface and an opposing second planar surface, and distal portion of the seal can comprise a plunger. In some aspects, the plunger can extend from the radial flange 210 toward the distal end 204. The plunger can comprise a distal portion that is adjacent the distal end 204 of the adaptor body 200. The plunger can comprise a cylindrical or elongate shaft 222 extending from the second planar surface of the radial flange 210 and terminating in an annular edge. In some aspects, the annular edge comprises an annular head 224. The annular head 224 can have a cross-sectional thickness that is approximately equal to or greater than a cross-sectional thickness of a wall of the cylindrical shaft 222.

The seal 208 can include an access aperture 214 extending axially through the radial flange 210 from the first planar surface to the second planar surface. The access aperture 214 can be aligned with the longitudinal axis 900 of the adaptor body 200 so that an instrument or device being advanced or retracted through the passageway remains axially aligned with longitudinal axis 900. In some aspects, movement of an instrument or device, transverse to the longitudinal axis 900, is restricted by the seal 208. In some embodiments, the access aperture 214 comprises a cross-sectional width that is approximately equal to or less than the cross-sectional width of the suction catheter tube 11 to create a friction fit between the suction catheter tube 11 and the seal 208.

The cylindrical shaft 222 can extend around the access aperture 214 such that an inner surface of the seal 208 forms a passageway extending from the access aperture 214 to the annular head 224. The inner surface of the cylindrical shaft 222 can comprise a cross-sectional width that is greater than the cross-sectional width of the access aperture 214. The outer surface of the cylindrical shaft 222 can comprise a cross-sectional width that is approximately equal to less than an inner surface of the distal portion of the adaptor body 200.

The seal 208 can include a fluid aperture 226 extending radially through a wall of the cylindrical shaft 222. In some aspects, the seal 208 comprises a plurality of fluid apertures 226. The fluid aperture 226 is configured to provide a passage between an area adjacent to the outer surface of the plunger, and an area adjacent to the inner surface of the plunger. In some aspects, the fluid aperture 226 can comprise any of a hole, slot, a mesh, and other features that permit a fluid to pass between the inner and outer surfaces of the plunger.

The seal 208 can comprise a resilient or flexible material (e.g., an elastomeric material). In some aspects, the seal 208 comprises portions having different rigidity. In some examples, the radial flange 210 can comprise an elastomeric material, and any of the cylindrical shaft 222 and annular head 224 can comprise a material with a greater axial rigidity than the radial flange 210.

In some embodiments, the proximal portion of the seal 208 can comprise a flange member that extends radially outward, from the longitudinal axis 900 toward the inner surface of the adaptor body 200. The flange member can comprise any of a disk, an arm, and a mesh. A distal portion of the seal 208 can comprise a plunger member that extends toward the distal end 204 of the adaptor body 200. The plunger member can comprise any of a cylindrical tube, an arm, and a mesh. In some aspects, a distal portion of the plunger member extends beyond the distal end 204 of the adaptor body 200.

Figure 6:
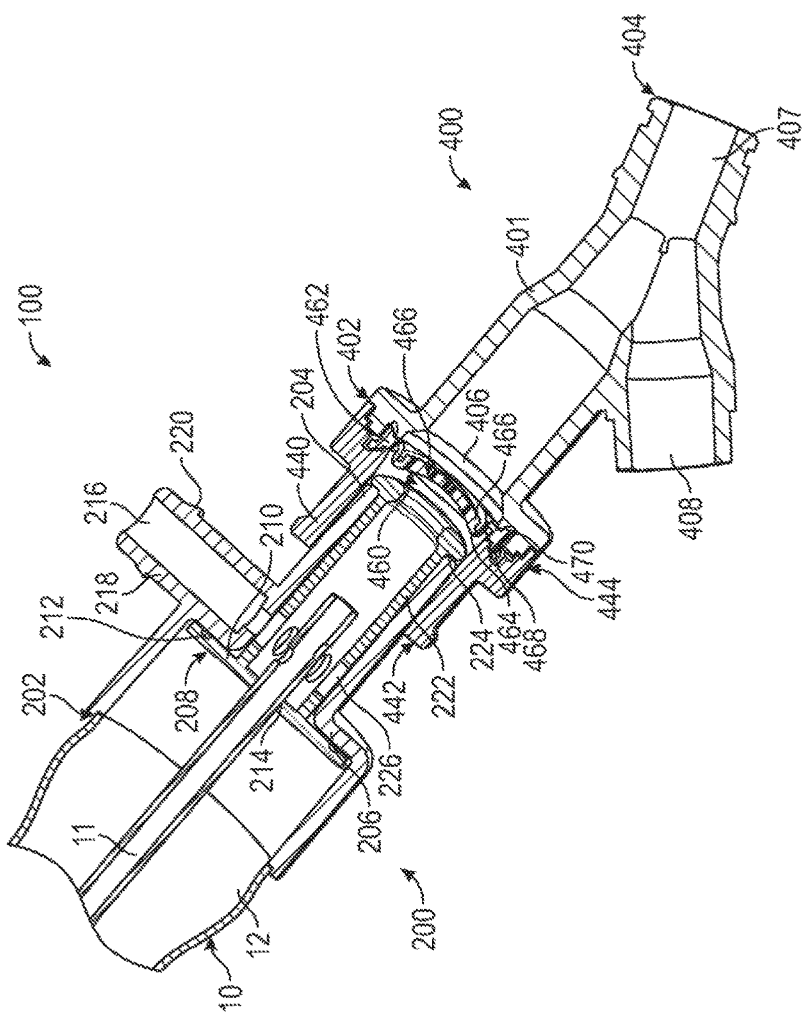
FIGS. 6-9 illustrate cross-sectional views of the suction catheter adaptor of FIG. 4.

Referring now to FIG. 6, the radial flange 210 of the seal 208 is positioned in the passageway between the proximal end 202 and the distal end 204. The radial flange 210 can extend across the passageway between the proximal end 202 and the distal end 204. The radial flange 210 can engage or seat against the circumferential ledge 206. In some aspects, the seal 208 is coupled to the adaptor body 200 at a connection region 212 between the radial flange 210 and the adaptor body 200. The connection region 212 can be between planar portions of the radial flange 210 and the circumferential ledge 206. The connection region 212 can comprise any of a mechanical fastener, an adhesive, welding, or another coupling method. The access aperture 214 of the seal 208 can be aligned with the longitudinal axis 900 of the adaptor body 200 so that an instrument or device being advanced or retracted through the passageway remains in alignment with a valve in the airway adaptor 400.

With the radial flange 210 seated against the circumferential ledge 206, the cylindrical shaft 222 extends from the radial flange 210 toward the distal end 204 of the adaptor body 200. A portion of the cylindrical shaft 222 can extend beyond the distal end 204 of the adaptor body 200, terminating at the annular head 224. A portion of the plunger, e.g., the cylindrical shaft 222, forms a wash zone in the adaptor body 200 between the radial flange 210 and the annular head 224.

In some embodiments, the adaptor body 200 can include a radial port 216 forming a passageway through a wall of the adaptor body 200, between the radial flange 210 and the distal end 204. In some aspects, the radial port 216 forms an elongate body 218 extending radially from the outer surface of the adaptor body 200. The radial port 216 is in fluid communication with the passageway of the adaptor body 200. The radial port 216 can be configured to provide a fluid for cleaning operations to be described in detail herein. An outer surface of the elongate body 218 can include an engagement member to permit fluidly coupling the radial port 216 with any of any of a tube, caps, and nozzle. The engagement member can comprise an outwardly extending ridge 220 for engagement with certain implements such as a fluid tube 14, caps, solution nozzles and the like (FIG. 1).

Still referring to FIG. 6, the adaptor body 200 can be coupled with an airway adaptor 400. The airway adaptor 400 includes a housing 401 with a plurality of openings and an inner surface defining a passageway between the plurality of openings. In some embodiments, a first opening at a proximal end 402 of the housing 401 forms an access port 406 configured to couple with the adaptor body 200 and receive an instrument, such as the suction catheter tube 11, into the passageway. A second opening at an opposing distal end 404 of the housing 401 forms a respiratory port 407 configured to couple with an artificial airway of a patient. A third opening, between the proximal end 402 and the distal end

404, forms a ventilator port 408 configured to couple with a ventilator to provide respiratory gas to the patient.

The airway adaptor 400 can include a collar 440 having a first end 442, an opposing second end 444, and a passageway between the first end 442 and the second end 444. The second end 444 of the collar 440 is coupled to the proximal end 402 of the housing 401. The second end 444 is configured to couple with the housing 401 using any of a mechanical fastener, an adhesive, welding, or another coupling method. In some embodiments, the collar 440 and housing 401 are formed together as a unitary component. In some aspects, the collar 440 extends along an axial length of the access port 406. The inner surface of the passageway of the collar 440 can comprise a cross-sectional width that is approximately equal to or greater than the cross-sectional width of the outer surface of the adaptor body 200. The first end 442 of the collar 440 receives the distal end 204 of the adaptor body 200 into the passageway of the collar 440.

Figure 7:
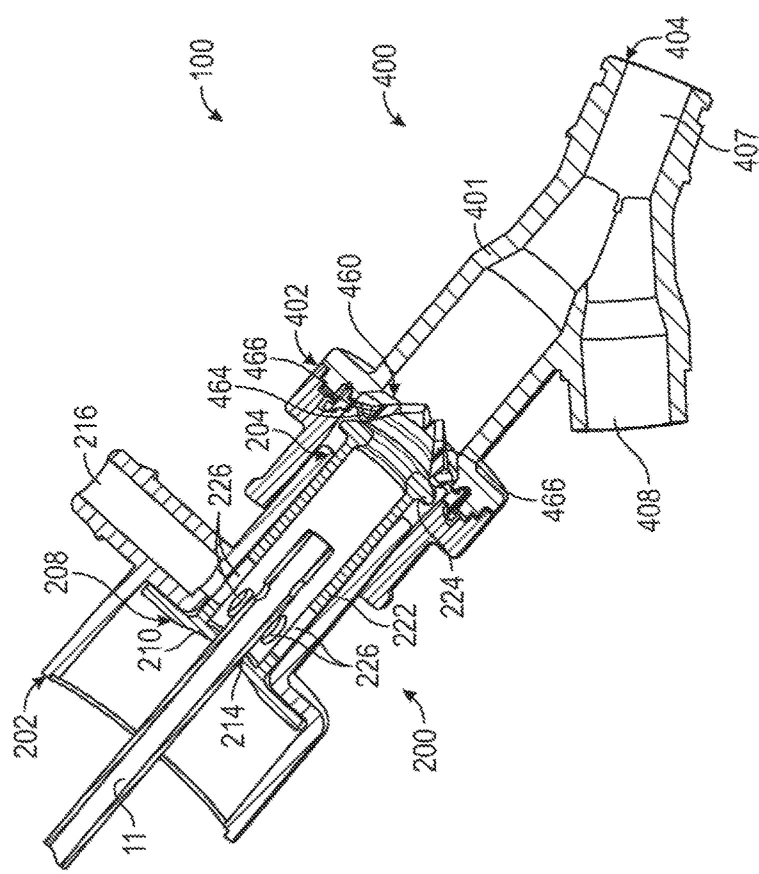

The airway adaptor 400 includes a valve 460 having a first orientation (FIG. 6) and a second orientation (FIG. 7). In the first orientation, the valve 460 can be configured to fluidly isolate the passageway of the collar 440 from a passageway between the ventilator port 408 and the respiratory port 407. In some embodiments, the passageway of the collar 440 is partially isolated in the first orientation. The valve 460, in a second orientation, can be open to fluidly couple the passageway of the collar 440 with the passageway between the ventilator port 408 and the respiratory port 407. In the second orientation, the valve can permit an instrument or other device to be inserted into the airway adaptor 400.

In some aspects, the valve comprises a rim 462, a resiliently flexible annular ridge 464, and a plurality of valve segments 466 that are moveable relative to each other. The valve segments 466 can be separated by any of a cut, an opening, and a slit. The rim 462 forms the outer circumferential surfaces of the valve 460. The rim 462 includes a first or leading edge 468 and an opposing second or trailing edge 470. The rim 462 is positioned in a valve retention structure between the collar 440 and the housing 401. In some embodiments, the valve retention structures is an annular channel formed between the second end 444 of the collar 440 and the proximal end 402 of the housing 401. The valve 460 can be retained in the channel such that the leading edge 468 of the rim 462 engages the second end 444 of the collar 440, and the trailing edge 470 of the rim 462 engages the proximal end 402 of the housing 401. However, other valve retention structures are contemplated, for example, a rim-receiving member within the collar 440 proximal to the second end 444, or a series of apertures disposed around a rim 462 of the valve 460 for engagement with a corresponding structure within the housing 401 or collar 440, or for bonding to the housing 401 or collar 440.

In some aspects, the resiliently flexible annular ridge 464 is radially inward from the rim 462. The annular ridge 464 can form a convex surface projecting from a first surface of the valve 460 that is coplanar with the leading edge 468. The plurality of valve segments 466 extend radially inward from the annular ridge 464. The valve segments 466 can be separated by one or more slits that extend through the valve 460, from the first surface to a second surface that is coplanar with the trailing edge 470 of the valve 460. The annular ridge 464 and plurality of valve segments 466 can be configured such that the plurality of valve segments 466 occlude the passageway through the access port 406 when the valve 460 is in the first orientation. In a second orientation, the annular ridge 464 and plurality of valve segments 466 are biased or displaced to permit a fluid, instrument, or other device through the passageway.

The adaptor body 200 is coupled with the airway adaptor 400 by inserting the distal end 204 of the adaptor body 200 through the passageway of the collar 440. In some aspects, the adaptor body 200 is inserted a distance into the airway adaptor 400 such that the distal end 204 of the adaptor body 200 and the annular head 224 of the plunger remain separated from the valve 460. An instrument 10, coupled with the proximal end 402 of the airway adaptor 400 (FIG. 3), can include a suction catheter tube 11 surrounded by a sheath 12. The suction catheter tube 11 can be inserted through the access aperture 214 of the seal 208. During advancement or retraction of the suction catheter tube 11, the seal 208 can guide the suction catheter tube 11 relative to the longitudinal axis 900 of the adaptor body 200.

Referring to FIG. 7, the suction catheter adaptor 100 is illustrated during advancement of the suction catheter tube 11 through the access aperture 214 of the seal 208 toward the airway adaptor 400. The seal 208 is moved to engage and open the valve 460 to fluidly couple the access port 406 passageway with the adaptor body 200 passageway. In some aspects, the flange 210 is deformed such that a distal portion of the seal 208 engages the valve 460. The open valve 460 permits an instrument or other device to be inserted into the airway adaptor 400 with minimal or no obstruction.

In some aspects, the friction fit between the suction catheter tube 11 and the seal 208 causes an inner portion of the radial flange 210 to deflect or deform and shift toward the distal end 204 of the adaptor body 200 during advancement of the suction catheter tube 11. The plunger, which extends from the radial flange 210, is moved with the radial flange 210. In some aspects, the cylindrical shaft 222 of the plunger can be shifted toward the valve 460 a distance such that the annular head 224 engages the annular ridge 464 of the valve 460. Additional advancement of the suction catheter tube 11 with the annular head 224 engaged against the annular ridge 464 can urge or deflect the valve segments 466 into the housing 401 to place the valve 460 into the open or second orientation. In the second orientation, the opening provided by biased valve segments permits the suction catheter tube 11 to be advanced toward the distal end 204. The valve 460 can prevent or limit undesired transfer of air from the ventilator through the access port 406 while the suction catheter tube 11 extends through the valve 460.

Figure 8:
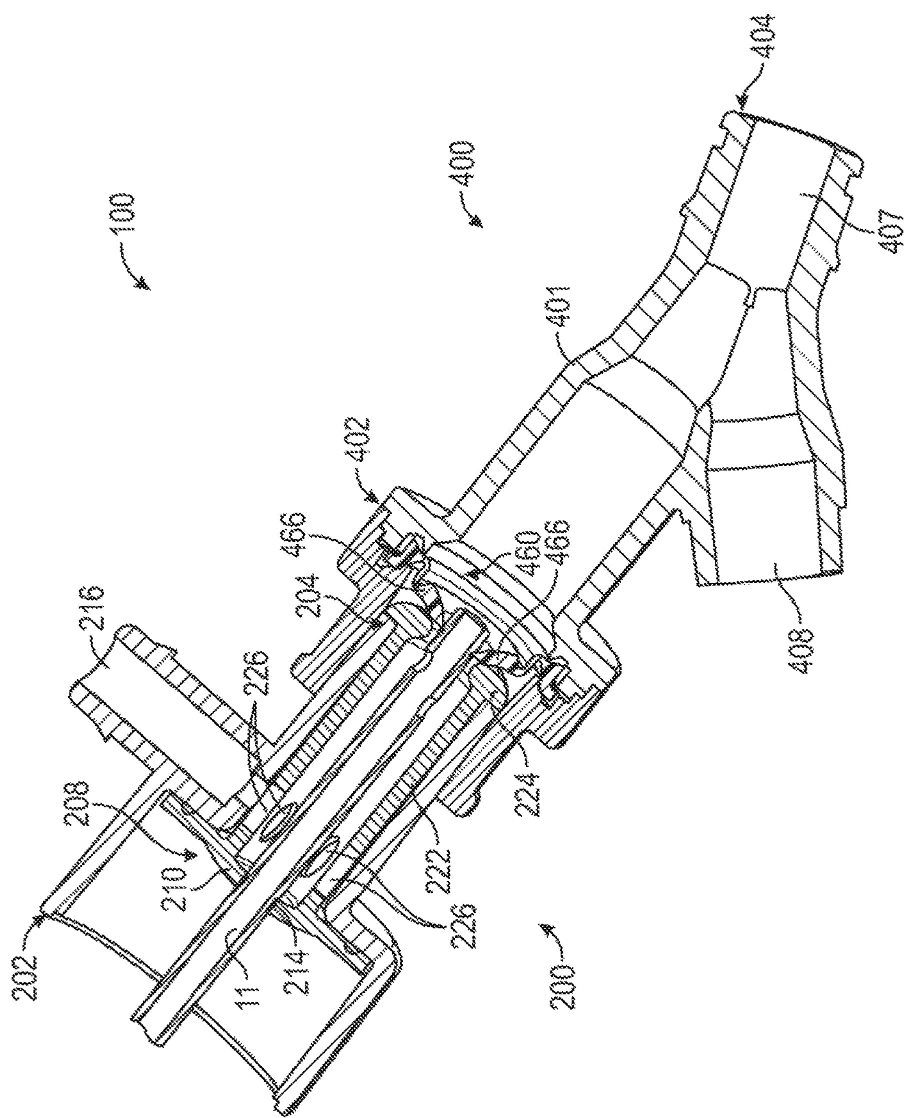

Referring to FIG. 8, the suction catheter adaptor 100 is illustrated during retraction of the suction catheter tube 11 from the airway adaptor 400. As the suction catheter tube 11 is retracted through the valve 460, the friction fit between the suction catheter tube 11 and the seal 208 causes the inner portion of the radial flange 210 to deflect or deform and shift toward the proximal end 202 of the adaptor body 200. Movement of the cylindrical shaft 222 with the radial flange 210 toward the proximal end 202 of the adaptor body 200 disengages the annular head 224 from the annular ridge 464 of the valve 460. As the suction catheter tube 11 is retracted through the valve 460, friction between the valve segments 466 and the suction catheter tube 11 deflects and inverts the valve segments 466 toward the first end 442 of the collar 440. Because the valve segments 466 are permitted to deflect and invert toward the direction of travel of the suction catheter tube 11, the force of the valve 460 against the suction catheter tube 11 is reduced.

Figure 9:
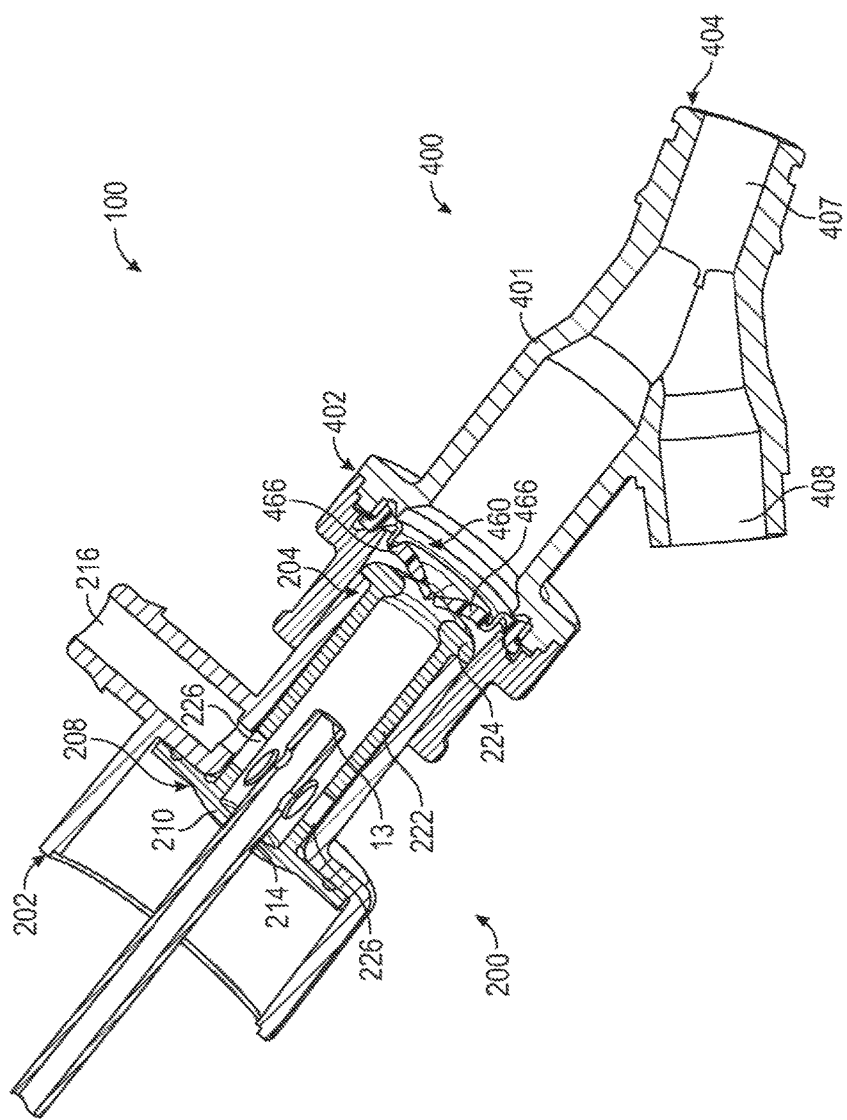

Referring to FIG. 9, the suction catheter adaptor 100 is illustrated with a tip 13 of the suction catheter tube 11 in the wash zone of the adaptor body 200, between the radial flange 210 and the annular head 224. Because the suction catheter tube 11 is withdrawn from the valve 460 and the annular head 224 is disengaged from the annular ridge 464, the annular ridge and the valve segments 466 readily return to an undeflected position in the airway adaptor 400 to occlude the passageway through the access port 406.

To flush the instrument 10, a cleaning fluid, such as saline, can be directed through the radial port 216 toward the passageway of the adaptor body 200. In some embodiments, the fluid apertures 226 extending through a wall of the cylindrical shaft 222 permit the cleaning fluid to be directed into the plunger of the seal 208. A suction force can be applied through the suction catheter to remove the cleaning fluid and contamination from the outer surface of the suction catheter tube 11 by the radial flange 210. Although the valve segments 466 return to an undeflected position to occlude the passageway, the valve 460 is configured to entrain or allow a small amount of airflow from the ventilator (relative to the amount and flow generated by a ventilation source of a particular patient's artificial airway circuit) through the valve 460. The entrained airflow is directed into the wash zone to agitate the cleaning fluid and improve the effectiveness of the cleaning procedure. In some aspects, the valve segments 466 return to an undeflected position to occlude the passageway when the suction force is ceased.

Figures 10A, 10B:
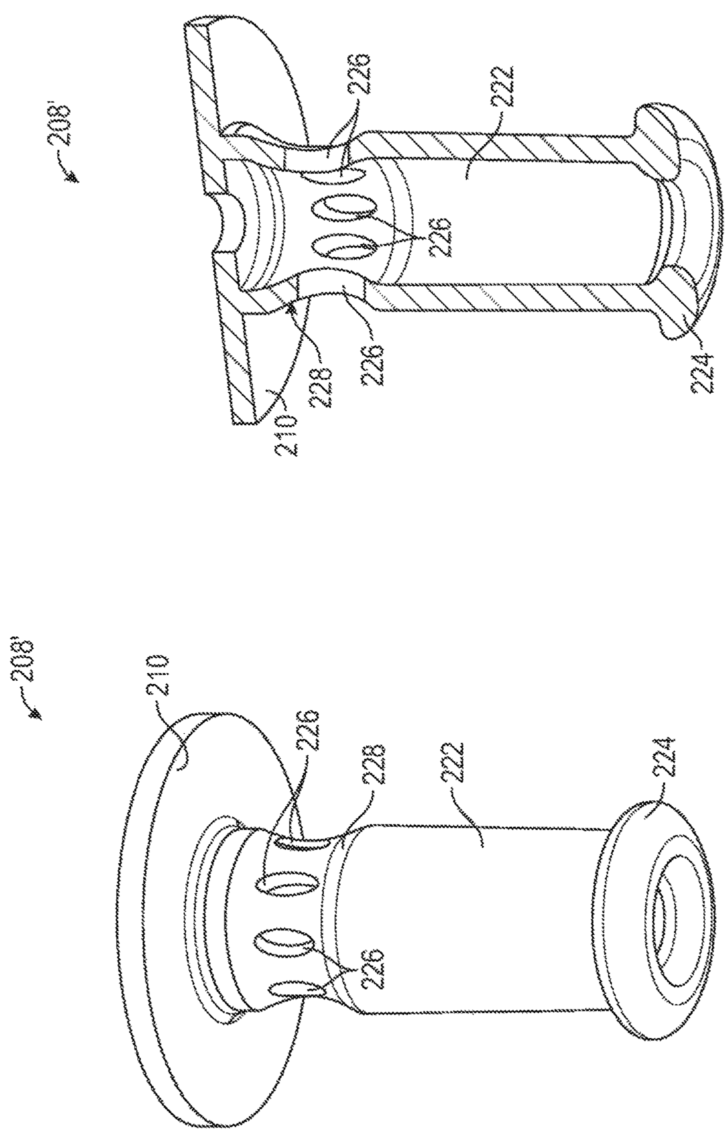
FIG. 10A illustrates a detail view a suction catheter adaptor, in accordance with aspects of the present disclosure.
FIG. 10B illustrates a cross-sectional view of the suction catheter adaptor of FIG. 10A.

Referring to FIGS. 10A-10B, embodiments of a seal 208' are illustrated in isolation. The seal 208' comprises a radial flange 210 having a first planar surface and an opposing second planar surface, and a plunger. The plunger comprises a cylindrical shaft 222 extending from the second planar surface of the radial flange 210 and terminating in an annular head 224. The seal 208' also includes an access aperture 214 extending through the radial flange 210 from the first planar surface to the second planar surface. An inner surface of the seal 208' forms a passageway extending from the access aperture 214, along the plunger, to the annular head 224.

In some aspects, the seal 208' also includes a fluid aperture 226 extending through a wall of the cylindrical shaft 222. In some embodiments, the seal 208' includes a plurality of fluid apertures 226 extending radially and aligned along a circumference of the cylindrical shaft 222. The fluid aperture 226 can comprise any of a hole, slot, a mesh, and other passage features that permit a fluid to move between the inner and outer surfaces of the plunger. In some aspects, the fluid aperture 226 comprises a hole with any of a round, oval, square, regular, and irregular perimeter.

The cylindrical shaft 222 can include a concaved outer surface 228. In some aspects, the concaved outer surface 228 extends along a circumference of the cylindrical shaft 222, forming a circumferential concave channel. The concaved outer surface 228 and the plurality of fluid apertures 226 can be axially aligned such that the fluid apertures 226 extend along the circumferential concave channel. In some aspects, the wall of the cylindrical shaft 222 is concaved radially inward such that an inner surface of the wall comprises an annular convex surface. In some aspects, the radial flange 210 can comprise an elastomeric material, and the cylindrical shaft 222 and annular head 224 can comprise a material with a greater rigidity than the radial flange 210.

Figure 11:
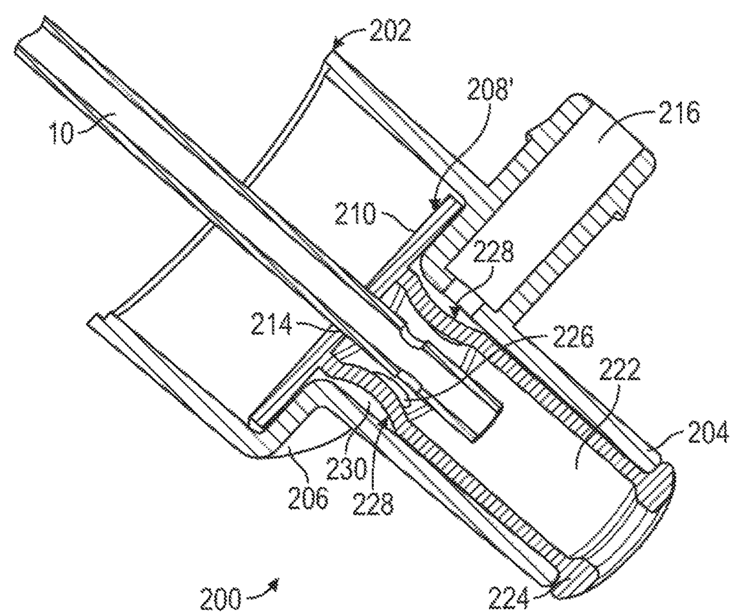
FIG. 11 illustrates a cross-sectional view of a suction catheter adaptor, in accordance with aspects of the present disclosure.

FIG. 11 illustrates the seal 208' of FIGS. 10A-10B within an adaptor body 200 as described above. An annular fluid passageway 230 is defined between the concaved outer surface 228 and the inner surface of the adaptor body 200. A cleaning fluid can be directed into the adaptor body 200 through the radial port 216. The annular fluid passageway 230 directs the cleaning fluid around the outer surface of the cylindrical shaft 222 where it is permitted to travel through the plurality of fluid apertures 226 into a wash zone between the radial flange 210 and the annular head 224.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. A suction catheter adaptor assembly comprising: an adaptor body comprising an inner surface defining a passageway between a proximal end and a distal end of the adaptor body, the distal end of the adaptor body configured to couple with an airway adaptor; and the airway adaptor comprising (i) an inner surface defining a passageway between a proximal end and a distal end of the airway adaptor, the distal end configured to couple with an artificial airway, and (ii) a valve configured to occlude the passageway, the valve comprising a resiliently flexible annular member and a plurality of valve segments separated by a slit; wherein, the distal end of the adaptor body, when received into the proximal end of the airway adaptor, engages the ridge to bias the plurality of valve segments toward the distal end of the airway adaptor such that the slit is expanded to fluidly couple the airway adaptor passageway and adaptor body passageway through the valve.

Concept 2. The suction catheter adaptor assembly of concept 1 or any preceding concept, wherein the adaptor body comprises a seal across the passageway proximal to the adaptor body distal end.

Concept 3. The suction catheter adaptor assembly of concept 2 or any preceding concept, wherein the seal comprises a radial flange with an access aperture, the access aperture of the seal having an inner surface with a cross-sectional width that is equal to or less than a cross-sectional width of an outer surface of a suction catheter inserted through the access aperture.

Concept 4. The suction catheter adaptor assembly of concept 1 or any preceding concept, wherein the valve comprises a plurality of slits.

Concept 5. The suction catheter adaptor assembly of concept 1 or any preceding concept, wherein the plurality of valve segments extends radially inward from the annular member.

Concept 6. The suction catheter adaptor assembly of concept 1 or any preceding concept, wherein the annular member comprises an annular continuous ridge.

Concept 7. A suction catheter adaptor assembly comprising: an adaptor body having a seal, the adaptor body comprising an inner surface defining a passageway between a proximal end and a distal end of the adaptor body, the distal end of the adaptor body configured to couple with an airway adaptor, the seal configured to extend across the passageway, the seal comprising (i) a radial flange having an access aperture, and (ii) a plunger comprising a cylindrical shaft extending distally from the radial flange toward the distal end of the adaptor body and terminating in an annular edge, wherein deflection of the radial flange toward the distal end of the adaptor body moves the plunger away from the proximal end of the adaptor body; and the airway adaptor comprising an inner surface defining a passageway between a proximal end and a distal end of the airway adaptor, the distal end configured to couple with an artificial airway, and a valve configured to occlude the passageway, the valve comprising a resiliently flexible annular member and a plurality of valve segments separated by a slit; wherein, when the adaptor body is coupled with the proximal end of the airway adaptor, deflection of the radial flange toward the distal end of the adaptor body engages the annular edge of the plunger against the annular member of the airway adaptor valve, such that the plurality of valve segments are deflected toward the distal end of the airway adaptor to open the slit and fluidly couple the airway adaptor passageway and adaptor body passageway.

Concept 8. The suction catheter adaptor assembly of concept 7 or any preceding concept, wherein deflection of the radial flange toward the proximal end of the adaptor body retracts the plunger toward the proximal end of the adaptor body.

Concept 9. The suction catheter adaptor assembly of concept 7 or any preceding concept, wherein the access aperture of the seal comprises an inner surface with a cross-sectional width that is equal to or less than a cross-sectional width of an outer surface of a suction catheter inserted through the access aperture.

Concept 10. The suction catheter adaptor assembly of concept 9 or any preceding concept, wherein retraction of a suction catheter inserted through the access aperture of the seal toward the proximal end of the adaptor body retracts the head from the annular member of the valve.

Concept 11. The suction catheter adaptor assembly of concept 9 or any preceding concept, wherein retraction of a suction catheter inserted through the valve and towards the proximal end of the adaptor body shifts the valve segments toward the adaptor body.

Concept 12. The suction catheter adaptor assembly of concept 7 or any preceding concept, wherein the adaptor body comprises a radial port between the seal and the distal end of the adaptor body, the radial port having a passageway fluidly coupled to the passageway of the adaptor body.

Concept 13. The suction catheter adaptor assembly of concept 12 or any preceding concept, wherein a fluid aperture extends through a wall of the cylindrical shaft such that the radial port is fluidly coupled to an inner surface of the cylindrical shaft.

Concept 14. The suction catheter adaptor assembly of concept 13 or any preceding concept, wherein a plurality of fluid apertures extends through the wall about a circumference of the cylindrical shaft.

Concept 15. The suction catheter adaptor assembly of concept 7 or any preceding concept, wherein the outside surface of the cylindrical shaft is concaved, forming a concave channel about a circumference of the shaft.

Concept 16. The suction catheter adaptor assembly of concept 15 or any preceding concept, wherein the concave channel, and a fluid aperture extending through a wall of the cylindrical shaft are axially aligned between the radial flange and the annular edge.

Concept 17. The suction catheter adaptor assembly of concept 7 or any preceding concept, wherein the annular edge comprises an annular head, the annular head having a cross-sectional thickness greater than a cross-sectional thickness of a wall of the cylindrical shaft.

Concept 18. A method of fluidly coupling a suction catheter using a suction catheter adaptor, comprising: advancing an adaptor body into a passageway of an airway adaptor such that a distal end of the adaptor body engages a valve within the airway adaptor, the valve comprising a resiliently flexible annular member and a plurality of valve segments defined by a slit; and advancing the distal end of the adaptor body distally against the annular member such that the plurality of valve segments are deflected distally away from the distal end of the adaptor body to fluidly couple a passageway through the adaptor body with the airway adaptor distally of the valve.

Concept 19. The suction catheter adaptor assembly of concept 18 or any preceding concept, further comprising advancing a suction catheter through the passageway of the adaptor body and the passageway of the airway adaptor, the suction catheter being permitted to pass between the biased plurality of valve segments.

Concept 20. A method of fluidly coupling a suction catheter adaptor, comprising: coupling a distal end of an adaptor body with a passageway of an airway adaptor having a valve comprising a plurality of valve segments defined by a slit, the adaptor body comprising seal having a radial flange and a plunger, the plunger comprising a cylindrical shaft extending from the radial flange toward the distal end of the adaptor body and terminating in an annular edge; biasing the radial flange toward the distal end of the adaptor body to move the plunger into engagement with the valve; and advancing the plunger against the valve to bias the plurality of valve segments away from the adaptor body.

Concept 21. The suction catheter adaptor assembly of concept 20 or any preceding concept, further comprising biasing the radial flange by advancing a suction catheter through an access aperture of the seal, wherein the access aperture comprises an inner surface with a cross-sectional width is equal to or less than a cross-sectional width of an outer surface of the suction catheter.

It is understood that any specific order or hierarchy of blocks in the processes disclosed is an illustration of example approaches. Based upon design or implementation preferences, it is understood that the specific order or hierarchy of blocks in the processes may be rearranged, or that all illustrated blocks be performed. In some implementations, any of the blocks may be performed simultaneously.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A suction catheter adaptor assembly comprising:

an adaptor body having a seal, the adaptor body comprising an inner surface defining a passageway between a proximal end and a distal end of the adaptor body, the distal end of the adaptor body configured to couple with an airway adaptor, the seal comprising a flexible radial flange and a plunger, the radial flange intersecting the passageway and having an access aperture therethrough, and the plunger comprising a cylindrical shaft extending distally from the radial flange toward the distal end of the adaptor body, wherein deflection of the radial flange toward the distal end of the adaptor body moves the plunger, relative to the adaptor body, toward the distal end of the adaptor body; and an airway adaptor comprising (i) an inner surface defining a passageway between a proximal end and a distal end of the airway adaptor, the distal end configured to couple with an artificial airway, and (ii) a valve configured to occlude the passageway, the valve comprising a resiliently flexible annular member and a plurality of valve segments separated by a slit;

wherein, when the adaptor body is coupled with the proximal end of the airway adaptor, deflection of the radial flange toward the distal end of the adaptor body engages a distal end portion of the plunger against the annular member to bias the plurality of valve segments toward the distal end of the airway adaptor such that the slit is expanded to fluidly couple the airway adaptor passageway and adaptor body passageway through the valve.

2. The suction catheter adaptor assembly of claim 1, wherein the seal extends across the passageway proximal to the adaptor body distal end.

3. The suction catheter adaptor assembly of claim 2, wherein the access aperture of the seal comprises an inner surface with a cross-sectional width that is equal to or less than a cross-sectional width of an outer surface of a suction catheter inserted through the access aperture.

4. The suction catheter adaptor assembly of claim 1, wherein the valve comprises a plurality of slits.

5. The suction catheter adaptor assembly of claim 1, wherein the plurality of valve segments extends radially inward from the annular member.

6. The suction catheter adaptor assembly of claim 1, wherein the annular member comprises an annular continuous ridge.

7. A suction catheter adaptor assembly comprising:

an adaptor body having a seal, the adaptor body comprising an inner surface defining a passageway between a proximal end and a distal end of the adaptor body, the distal end of the adaptor body configured to couple with an airway adaptor, the seal configured to extend across the passageway, the seal comprising (i) a flexible radial flange having an access aperture, and (ii) a plunger comprising a cylindrical shaft extending distally from the radial flange toward the distal end of the adaptor body and terminating in an annular edge, wherein deflection of the radial flange toward the distal end of the adaptor body moves the plunger, relative to the adaptor body, toward the distal end of the adaptor body; and the airway adaptor comprising an inner surface defining a passageway between a proximal end and a distal end of the airway adaptor, the distal end configured to couple with an artificial airway, and a valve configured to occlude the passageway, the valve comprising a resiliently flexible annular member and a plurality of valve segments separated by a slit;

wherein, when the adaptor body is coupled with the proximal end of the airway adaptor, deflection of the radial flange toward the distal end of the adaptor body engages the annular edge against the annular member of the airway adaptor valve, such that the plurality of valve segments are deflected toward the distal end of the airway adaptor to open the slit and fluidly couple the airway adaptor passageway and adaptor body passageway.

8. The suction catheter adaptor assembly of claim 7, wherein deflection of the radial flange toward the proximal end of the adaptor body retracts the plunger toward the proximal end of the adaptor body.

9. The suction catheter adaptor assembly of claim 7, wherein the access aperture of the seal comprises an inner surface with a cross-sectional width that is equal to or less than a cross-sectional width of an outer surface of a suction catheter inserted through the access aperture.

10. The suction catheter adaptor assembly of claim 9, wherein retraction of a suction catheter inserted through the access aperture of the seal toward the proximal end of the adaptor body retracts the annular edge from the annular member of the valve.

11. The suction catheter adaptor assembly of claim 9, wherein retraction of a suction catheter inserted through the valve and towards the proximal end of the adaptor body shifts the valve segments toward the adaptor body.

12. The suction catheter adaptor assembly of claim 7, wherein the adaptor body comprises a radial port between the seal and the distal end of the adaptor body, the radial port having a passageway fluidly coupled to the passageway of the adaptor body.

13. The suction catheter adaptor assembly of claim 12, wherein a fluid aperture extends through a wall of the cylindrical shaft such that the radial port is fluidly coupled to an inner surface of the cylindrical shaft.

14. The suction catheter adaptor assembly of claim 13, wherein a plurality of fluid apertures extends through the wall about a circumference of the cylindrical shaft.

15. The suction catheter adaptor assembly of claim 7, wherein the outside surface of the cylindrical shaft is concaved, forming a concave channel about a circumference of the cylindrical shaft.

16. The suction catheter adaptor assembly of claim 15, wherein the concave channel, and a fluid aperture extending through a wall of the cylindrical shaft are axially aligned between the radial flange and the annular edge.

17. The suction catheter adaptor assembly of claim 7, wherein the annular edge comprises an annular head, the annular head having a cross-sectional thickness greater than a cross-sectional thickness of a wall of the cylindrical shaft.

18. A method of fluidly coupling a suction catheter adaptor, comprising:

coupling a distal end of an adaptor body with a passageway of an airway adaptor having a valve comprising a plurality of valve segments defined by a slit, the adaptor body comprising a seal having a flexible radial flange and a plunger, the plunger comprising a cylindrical shaft extending from the radial flange toward the distal end of the adaptor body and terminating in an annular edge;

biasing the radial flange toward the distal end of the adaptor body to move the plunger, relative to the adaptor body, toward the distal end of an adaptor body and into engagement with the valve; and advancing the plunger against the valve to bias the plurality of valve segments away from the adaptor body.

19. The method of claim 18, further comprising biasing the radial flange by advancing a suction catheter through an access aperture of the seal, wherein the access aperture comprises an inner surface with a cross-sectional width is equal to or less than a cross-sectional width of an outer surface of the suction catheter.

* * * * *